(12) United States Patent
Desai et al.

(10) Patent No.: US 9,027,405 B2
(45) Date of Patent: May 12, 2015

(54) ULTRASONIC INSPECTION OF AN AXLE

(71) Applicant: General Electric Company, Schenectady, NY (US)

(72) Inventors: Anand Hasmukh Desai, State College, PA (US); Garrett John Vidak, Lewistown, PA (US); Thomas William Lute, Jr., Middleburg, PA (US)

(73) Assignee: General Electric Company, Schenectady, NY (US)

( * ) Notice: Subject to any disclaimer, the term of this patent is extended or adjusted under 35 U.S.C. 154(b) by 151 days.

(21) Appl. No.: 13/682,148

(22) Filed: Nov. 20, 2012

(65) Prior Publication Data

US 2014/0137649 A1 May 22, 2014

(51) Int. Cl.
*G01N 29/26* (2006.01)
*G01N 29/06* (2006.01)
*G01N 29/22* (2006.01)
*G01N 29/24* (2006.01)
*G01N 29/265* (2006.01)
*G01N 29/27* (2006.01)

(52) U.S. Cl.
CPC ............ *G01N 29/26* (2013.01); *G01N 29/0645* (2013.01); *G01N 29/225* (2013.01); *G01N 29/2487* (2013.01); *G01N 29/262* (2013.01); *G01N 29/265* (2013.01); *G01N 29/27* (2013.01); *G01N 2291/106* (2013.01); *G01N 2291/2626* (2013.01)

(58) Field of Classification Search
USPC ..................... 73/602, 622, 623, 660
See application file for complete search history.

(56) References Cited

U.S. PATENT DOCUMENTS

| 5,426,978 | A | * | 6/1995 | Imai ................................ 73/622 |
| 8,336,383 | B2 | * | 12/2012 | Lesage et al. .................. 73/632 |
| 2006/0201253 | A1 | * | 9/2006 | Gonzales et al. ............... 73/643 |
| 2010/0031751 | A1 | | 2/2010 | Perkins et al. |
| 2010/0180683 | A1 | | 7/2010 | Lesage et al. |
| 2012/0144635 | A1 | | 6/2012 | Potje et al. |
| 2012/0191377 | A1 | | 7/2012 | Engl et al. |

FOREIGN PATENT DOCUMENTS

| JP | 2002257798 A | 9/2002 |
| JP | 2005283379 A | 10/2005 |

OTHER PUBLICATIONS

Erhard, A.; Bertus, N.; Montag, H.-J..; Schenk, G., "Ultrasonic Phased Array System for Railroad Axle Examination", Mar. 2003, NDT.net, vol. 8 No. 3, 6 pages.*
W. Hansen, H. Hintze, Ultrasonic Testing of Railway Axles With Phased Array Technique Experiences During Operation, GE Inspection Technologies, Hurth, Germany, 6 pages.
Dr. P N. Marty et al.; Latest Development in the UT Inspection of Train Wheels and Axles, 18th World Conference on Nondestructive Testing, Apr. 16-20, 2012, Durban, South Africa, 11 pages.
Search report from PCT/US2013/070767 dated Mar. 11, 2014.

* cited by examiner

*Primary Examiner* — Laura Martin
*Assistant Examiner* — Rose M Miller
(74) *Attorney, Agent, or Firm* — Hiscock & Barclay LLP

(57) ABSTRACT

A method and system for ultrasonic inspection of an axle is disclosed. An ultrasonic probe and wedge are placed on the radial surface of an outboard journal of the axle and an ultrasonic scan is directed toward the inboard journal, wherein the devices mounted on the inboard journal remain mounted during the ultrasonic scan.

18 Claims, 3 Drawing Sheets

ULTRASONIC INSPECTION OF AN AXLE

BACKGROUND OF THE INVENTION

The subject matter disclosed herein relates to a method and system for ultrasonic inspection of an axle.

Nondestructive testing devices can be used to inspect test objects to detect and analyze anomalies in the objects. Nondestructive testing typically involves placing one or more probes on the surface of the test object in order to perform testing of the underlying structure. One method of nondestructive testing employs ultrasonic signals.

Generally, an ultrasonic testing system includes an ultrasonic probe for transmitting and receiving ultrasonic acoustic waves to and from a test object, and a probe cable for connecting the ultrasonic probe to an ultrasonic test unit that includes a display for viewing the test results. In an ultrasonic testing system, electrical pulses are fed from the ultrasonic test unit to an ultrasonic probe where they are transformed into acoustic pulses by one or more ultrasonic transducers (e.g., piezoelectric elements) in the ultrasonic probe. During operation, electrical pulses are applied to the electrodes of one or more ultrasonic transducers, thus generating ultrasonic acoustic waves that are transmitted to the test object to which the probe is coupled. Conversely, when an ultrasonic acoustic wave is reflected from the test object and contacts the surface of the ultrasonic transducer(s), it causes the transducer(s) to vibrate, generating a voltage that is detected as a receive signal by the ultrasonic test unit. As the ultrasonic acoustic waves pass through the test object, various reflections, called echoes, occur as the ultrasonic acoustic wave interacts with anomalies within the test object.

When testing with a single element probe, the echo signals are typically displayed on the screen of the ultrasonic test unit as an A-scan trace with echo amplitudes appearing as vertical deflections of the trace and time of flight or distance information displayed on the horizontal axis along the trace. This single element probe is often mounted on a wedge to direct the sound at a desired angle to inspect different regions of the test object. In order to inspect the full volume of the object, it may be necessary to scan the object several times using different angled wedges, which can be time consuming.

Another type of ultrasonic probe, a phased array ultrasonic probe, has a plurality of electrically and acoustically independent ultrasonic transducers mounted in a single housing. By varying the timing of the electrical pulses applied to the ultrasonic transducers, a phased array ultrasonic probe can generate ultrasonic beams at different angles, allowing the phased array ultrasonic probe to steer the ultrasonic beam at different angles through the test object to try to detect anomalies using a single wedge. The ultrasonic waves received at the various angles can be processed to produce a sector scan (or S-scan) image of the test object, allowing visual identification of any anomalies, eliminating the need to rescan the test object several times with different wedges on a single element probe. The S-scan provides a two-dimensional view of all amplitude and depth data from all of the transducers of the phased array probe corrected for the delay and the refracted angle.

Ultrasonic probes are used to inspect axles of, e.g., railway cars. A typical rail axle will include seats for mounting rotating devices involved in the operation of the railway car, including wheels. The inboard journal of the rail axle located between the wheels typically includes one or more gears, brake discs, and a cover for protecting the axle. These devices located on the inboard journal of the rail axle make ultrasonic inspection of the inboard journal by placing one or more ultrasonic probes on the inboard journal difficult and time consuming. For example, the cover of the inboard journal must be removed or otherwise disassembled to provide access to the rail axle to place the ultrasonic probe in contact with the inboard journal.

The discussion above is merely provided for general background information and is not intended to be used as an aid in determining the scope of the claimed subject matter.

BRIEF DESCRIPTION OF THE INVENTION

A method and system for ultrasonic inspection of an axle is disclosed. An ultrasonic probe and wedge are placed on the radial surface of an outboard journal of the axle and an ultrasonic scan is directed toward the inboard journal, wherein the devices mounted on the inboard journal remain mounted during the ultrasonic scan. An advantage that may be realized in the practice of some disclosed embodiments of the method and system for ultrasonic inspection of an axle is that removal or disassembly of devices on the inboard journal of the axle is not required, simplifying and reducing the time required to conduct the inspection.

In one embodiment, a method for ultrasonic inspection of an axle is disclosed, wherein the axle comprises a longitudinal axis and an inboard journal between a first outboard journal and a second outboard journal, and wherein a plurality of devices are mounted on the inboard journal. The method comprises the steps of placing a first ultrasonic probe and a first ultrasonic wedge at a first location on a radial surface of the first outboard journal, wherein the radial surface is substantially parallel to the longitudinal axis of the axle, and performing a first ultrasonic scan directed to the inboard journal, wherein the plurality of devices mounted on the inboard journal remain mounted during the first ultrasonic scan.

In another embodiment, a system for ultrasonic inspection of an axle is disclosed, wherein the axle comprises a longitudinal axis and an inboard journal between a first outboard journal and a second outboard journal, and wherein a plurality of devices are mounted on the inboard journal. The system comprises an ultrasonic inspection station comprising a display, a microprocessor, a memory coupled to the microprocessor, and one or more executable instructions stored in the memory and configured to be executed by the processor, a first ultrasonic probe and a first ultrasonic wedge at a first location on a radial surface of the first outboard journal, wherein the radial surface is substantially parallel to the longitudinal axis of the axle, and a first probe cable connecting the first ultrasonic probe to the ultrasonic inspection station, wherein the first ultrasonic probe and the first ultrasonic wedge are configured to perform a first ultrasonic scan directed to the inboard journal, and wherein the plurality of devices mounted on the inboard journal remain mounted during the first ultrasonic scan.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
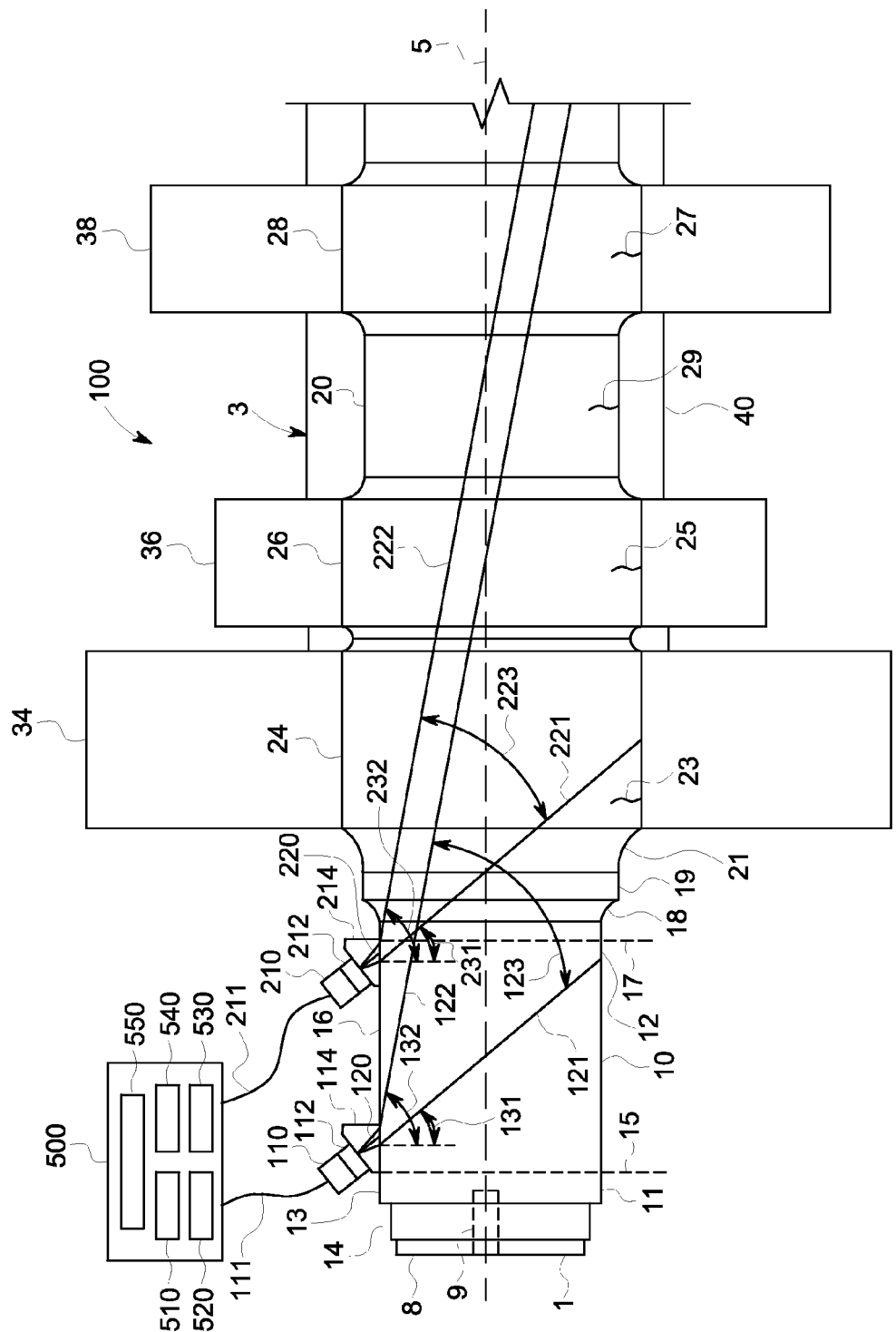
FIG. 1 is a block diagram of an exemplary ultrasonic testing system for inspecting an axle showing an enlarged view of the first end of the axle.
Figure 2:
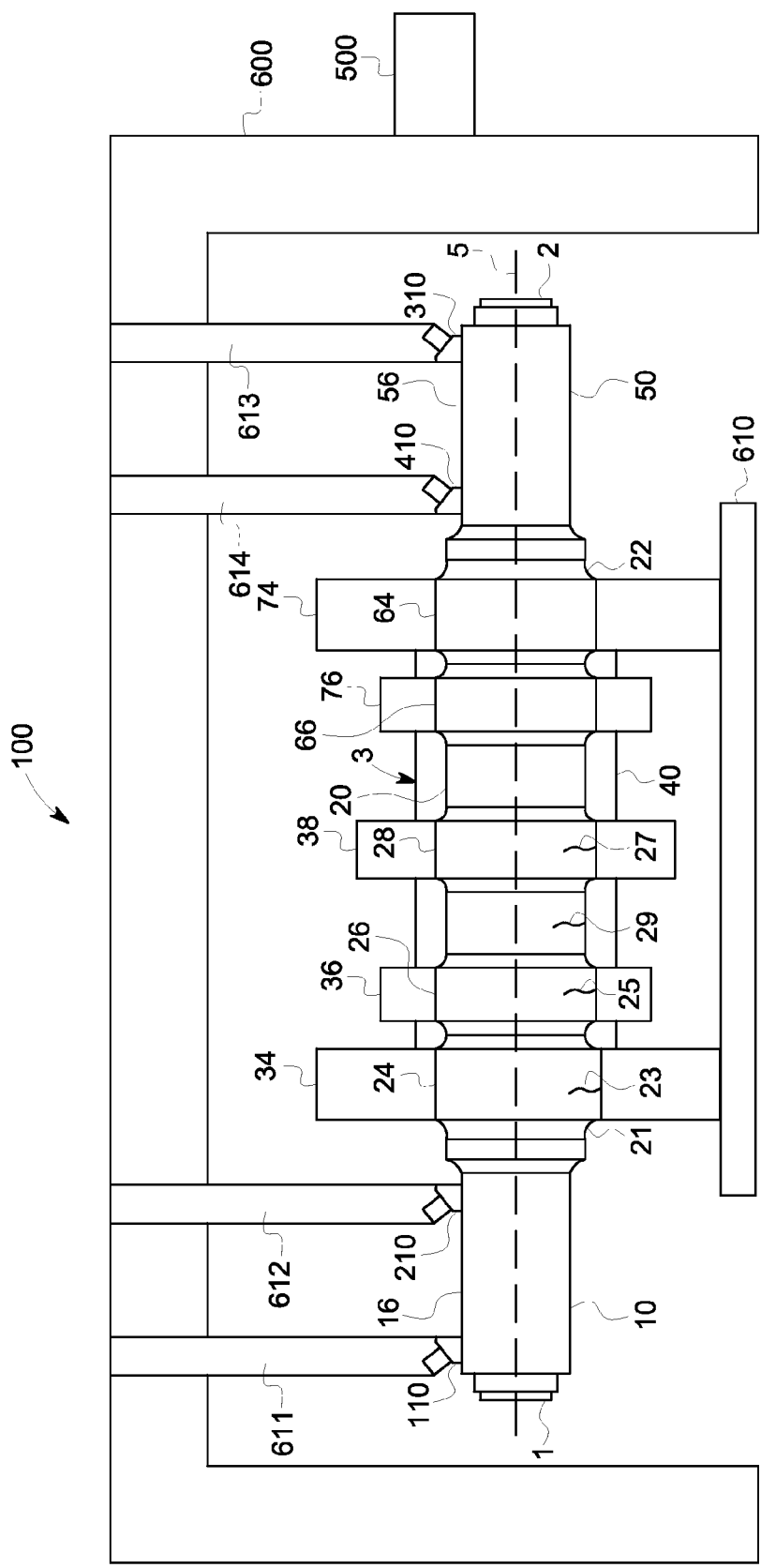
FIG. 2 is a block diagram of the exemplary ultrasonic testing system for inspecting the axle of FIG. 1 showing an exemplary inspection stand.

FIGS. 1 and 2 are block diagrams of an exemplary ultrasonic testing system 100 for inspecting an axle 3. FIG. 1 is an enlarged view of the first (left) end 1 of the axle 3. FIG. 2 shows the entire axle 3 (first end 1 and second (right) end 2) and an exemplary inspection stand 600. To illustrate the exemplary ultrasonic testing system 100, an exemplary axle 3 (e.g., a rail axle) is illustrated. It will be understood that the exemplary ultrasonic testing system 100 can be used with a variety of axles of different configurations.

The exemplary axle 3 includes a first (left) outboard journal 10 and a second (right) outboard journal 50 axially opposite of the first outboard journal 10, with an inboard journal 20 extending between the first outboard journal 10 and the second outboard journal 50. The first outboard journal 10 has a distal (first) end 11 and a proximal (second) end 12. The first end face 8 of the distal end 11 of the first outboard journal 10 can include a first end face opening 9 (e.g., counter sink or hollow shaft) extending through a portion of the first outboard journal 10 for mounting equipment. As shown in FIG. 1, the first outboard journal 10 may include multiple sections having different diameters with one or more steps 14 between the different sections. For example, a first end face step 14 can be located between the first end face 8 and the main portion 13 of the first outboard journal 10.

The inboard journal 20 of the axle 3 has a first end 21 proximate to the first outboard journal 10 and a second end 22 proximate to the second outboard journal 50. The axle 3 can include a first (left) wheel seat 24 for mounting a first (left) wheel 34 between the first outboard journal 10 and the inboard journal 20, and a second (right) wheel seat 64 for mounting a second (right) wheel 74 between the second outboard journal 50 and the inboard journal 20. The inboard journal 20 can also include a first (left) gear seat 26 for mounting a first (left) gear 36 and a second (right) gear seat 66 for mounting a second (right) gear 76. The inboard journal 20 can also include a brake disk seat 28 for mounting a brake disk 38. The inboard journal 20 may also include a cover (or cuff or sheath) 40 would need to be removed or otherwise disassembled to access the inboard journal 20. The first outboard journal 10 of the exemplary axle 3 also includes a curved step 18 between the main portion 13 and a dust (or water) guard seat 19.

The axle 3 is shown with various anomalies, including a first wheel seat anomaly 23, a first gear seat anomaly 25, a brake disk seat anomaly 27, and an inboard journal anomaly 29. An ultrasonic testing system 100 can be employed to detect the presence of these anomalies 23, 25, 27, 29.

The ultrasonic testing system 100 can comprise a first probe 110 mounted on a first ultrasonic wedge 114 and a second probe 210 mounted on a second ultrasonic wedge 214. It will be understood that the probe and a wedge can be provided as separate components or integrated into a single device. The first and second ultrasonic probes 110, 210 include a transducer element (for a single element ultrasonic probe) or transducer array (for a phased array ultrasonic probe) 112, 212. The first and second ultrasonic wedges 114, 214 can be made from any material that has an acoustic velocity different from that of the axle 3. For example, some ultrasonic wedges are made from plastics such as plexi-glass or a polystyrene material through which sound travels at a known velocity. In one embodiment, the first ultrasonic wedge 114 is located on the radial surface 16 (i.e., surface substantially parallel to the longitudinal axis 5 of the axle 3) of the first outboard journal 10 at a first ultrasonic wedge location 15 proximate to the distal end 11 of the first outboard journal 10, while a second ultrasonic wedge 214 is located on the radial surface 16 of the first outboard journal 10 at a second ultrasonic wedge location 17 proximate to the proximal end 12 of the first outboard journal 10. As shown in FIG. 2, the ultrasonic testing system 100 can also comprise a third ultrasonic probe 310 and a fourth ultrasonic probe 410 (and related devices (e.g., transducer array and ultrasonic wedges)) located on the radial surface 56 of the second outboard journal 50. While, for simplicity, the discussion of the ultrasonic testing system 100 focuses on the first and second ultrasonic probes 110, 210 located on the first outboard journal 10, it will be understood that the same discussion also applies to the third and fourth ultrasonic probes 310, 410 located on the second outboard journal 50.

One or more probe cables 111, 121 can connect the first and second ultrasonic probes 110, 210 to an ultrasonic inspection station 500, which can include one or more microprocessor(s) 510 for running system software and controlling system operations, and memory 520 coupled to the microprocessor 510. Computer program instructions (executable instructions) can be stored in memory 520 or available to be executed by the microprocessor 510 (e.g., downloadable from a network) can make up all or a portion of the software and software packages discussed herein. The ultrasonic inspection station 500 can also include a power supply 540, connected to an external power supply (e.g., AC voltage between 90V and 240V) or provided by rechargeable batteries. The ultrasonic inspection station 500 can also include peripheral interfaces 430 for managing data being sent between the ultrasonic inspection station 500 and other components. For example, in one embodiment, the peripheral interfaces 430 can include a USB, Ethernet (LAN), or wireless interface (WLAN) for receiving and loading an inspection plan.

The ultrasonic inspection station 500 can also comprise a display 550 for viewing system operations and inspection results. Electronics in the ultrasonic inspection station 500 can transmit and receive ultrasonic signals. The received signals are typically processed through some type of analog to digital conversion, after which they are displayed as A-scans with amplitude on the y axis and time of flight on the x axis (for single element ultrasonic probes) or displayed as sector scans (for phased array ultrasonic probes). These digital signals form the signature of a potential anomaly and are typically stored in memory 520 and post processed to provide additional views for the operator to assist in determining if an anomaly is truly a defect or not. The microprocessor 510 can provide control over the entire process.

In one embodiment and as shown in FIG. 2, the ultrasonic probes 110, 210, 310, 410 and the ultrasonic inspection station 500 can be part of an inspection stand 600 that includes a conventional roll stand 610 and a plurality (e.g., four) independently controlled ultrasonic probe manipulators 611, 612, 613, 614 for placing the ultrasonic probes 110, 210, 310, 410 onto the axle 3. The wheels 34, 74 of the axle 3 can be rotated by the roll stand 610 to provide a 360 degree ultrasonic scan of the axle 3 by the ultrasonic probes 110, 210, 310, 410 located on the outboard journals 10, 50. In another embodiment, axle 3 remains stationary while the ultrasonic probes 110, 210, 310, 410 are rotated around the axle 3 using the ultrasonic probe manipulators 611, 612, 613, 614.

As discussed previously, it is desirable to be able to perform an ultrasonic inspection of the inboard journal 20 of the axle 3 without having to remove or otherwise disassemble any of the devices mounted on the inboard journal 20, including the wheels 34, 74, gears 36, 76, brake disk 38, or cover 40. In one embodiment and as shown in FIG. 1, the first ultrasonic probe 110 and the second ultrasonic probe 210 can be phased array ultrasonic probes including ultrasonic transducer arrays 112, 212. It will be understood that other transducers (e.g., two-dimensional arrays and single elements) and wedges (different angles (e.g., in the range of thirty six degrees to forty four degrees) and materials) can be used. It will also be understood that, for clarity, while FIG. 1 only shows the ultrasonic inspection of the first end 1 of the axle 3 using ultrasonic probes 110, 210 located on the first outboard journal 10, additional ultrasonic probes can be located on the second outboard journal 50 for ultrasonic inspection of the entire axle 3. It will be further understood that in some embodiments, a single ultrasonic probe and ultrasonic wedge can be used in multiple locations on the axle 3 (rather than a plurality of probes 110, 120 and wedges 114, 214 simultaneously positioned at different locations along the axle 3). For example, a single phase array ultrasonic probe and ultrasonic wedge can be used in a single location on the first outboard journal 10 providing sufficient coverage of the first end 1 of the axle 3 from that one location and then relocated to the second outboard journal 50 to provide sufficient coverage of the second end 2 of the axle 3 from one location. Additionally, a single phase array ultrasonic probe and ultrasonic wedge can be used at a first location on the first outboard journal 10 and the moved to a second location on the first outboard journal 10. The single phase array ultrasonic probe and ultrasonic wedge can be slid axially from the first location to the second location. In the case where a single element ultrasonic probe is used with an ultrasonic wedge at a first location, the ultrasonic wedge can be changed several times to perform a complete scan of the axle from that first location.

Returning to FIG. 1, to conduct an ultrasonic inspection of the axle 3, the first ultrasonic wedge 114 and the second ultrasonic wedge 214 are located on the radial surface 16 of the main portion 13 of the first outboard journal 10. Locating the inspection devices on the first outboard journal 10 avoids having to remove or otherwise disassemble the cover 40 or any other devices to access the inboard journal 20 to place the ultrasonic wedges 114, 214 on the axle 3. Locating the inspection devices on the radial surface 16 of the first outboard journal 10 rather than the first end face 8 avoids having to compensate for or avoid engravings or other disruptions typically found on the first end face 8 of the axle 3 that can distort the ultrasonic inspection.

In the exemplary embodiment illustrated in FIG. 1, the material and angle of the first ultrasonic wedge 114 is chosen to provide a first incident ultrasonic beam 120 directed towards the inboard journal 20 that will produce a first ultrasonic beam sector scan 123 of the inboard journal 20 of the axle 3. The first ultrasonic beam sector scan 123 covers the range from a lower first refracted ultrasonic beam 121 (at a lower first refracted ultrasonic beam angle 131) to an upper first refracted ultrasonic beam 122 (at an upper first refracted ultrasonic beam angle 132). Similarly, the material and angle of the second ultrasonic wedge 214 is chosen to provide a second incident ultrasonic beam 220 directed towards the inboard journal 20 that will produce a second ultrasonic beam sector scan 223 of the inboard journal 20 of the axle 3. The second ultrasonic beam sector scan 223 covers the range from a lower second refracted ultrasonic beam 221 (at a lower second refracted ultrasonic beam angle 231) to an upper second refracted ultrasonic beam 222 (at an upper second refracted ultrasonic beam angle 232).

In one embodiment, the first ultrasonic probe 110 and the second ultrasonic probe 210 can be phased array ultrasonic probes including the same ultrasonic transducer arrays 112, 212 (e.g., 16 element, 2.25 MHz, linear phased array with 1.0 mm pitch). The ultrasonic wedges 114, 214 can be forty one degree wedges made of a cross linked polystyrene microwave plastic (REXOLITE). This combination (of the probe and wedge) can provide first and second ultrasonic beam sector scans 123, 223 within the range between a lower refracted ultrasonic beam angle 131, 231 of approximately forty degrees and an upper refracted ultrasonic beam angle 132, 232 of approximately eighty degrees to provide sufficient coverage to identify anomalies on the inboard journal as far as 75.0 cm or more away from the first end face 8. The ultrasonic beam sector scans 123, 223 can be performed at angular increments from 0.5 to 2.0 degrees. In the exemplary embodiment, the first ultrasonic probe 110 and transducer 112 are the same as the second ultrasonic probe 210 and transducer 212, and the first ultrasonic wedge 114 is the same as the second ultrasonic wedge 214, producing ultrasonic scans with the same parameters. In other embodiments, the first ultrasonic probe 110, transducer 112, and wedge 114 may be different from the second ultrasonic probe 210, transducer 212, and wedge 214.

In one embodiment, the first ultrasonic wedge location 15 on the radial surface 16 surface of the main portion 13 of the first outboard journal 10 can be determined by placing the first ultrasonic wedge 114 on the distal end 11 of the first outboard journal 10 as close to the first end face 8 without having the first ultrasonic beam sector scan 123 affected by the first end face opening 9 extending through a portion of the first outboard journal 10 or any first end face step 14 that may exist. Locating the first ultrasonic probe 110 and the first ultrasonic wedge 114 at the first ultrasonic wedge location 15 maximizes the coverage of the first ultrasonic beam sector scan 123 of the first outboard journal 10 and the first end 21 of the inboard journal 22. As can be seen in FIG. 1, the first ultrasonic beam sector scan 123 provides coverage from before the dust guard seat 19 well into the inboard journal beyond the brake disk seat 38, providing coverage of the first wheel seat anomaly 23, first gear seat anomaly 25, brake disk seat anomaly 27, and the inboard journal anomaly 29.

Similarly, the second ultrasonic wedge location 17 on the radial surface 16 of the main portion 13 of the first outboard journal 10 can be determined by placing the second ultrasonic wedge 214 on the proximal end 12 of the first outboard journal 10 as close to the first wheel seat 24 (or dust guard seat 19) without having the second ultrasonic beam sector scan 223 affected by any curved step 18 that may exist on the proximal end 12 of the first outboard journal 10. Locating the second ultrasonic probe 210 and the second ultrasonic wedge 214 at the second ultrasonic wedge location 17 maximizes the coverage of the second ultrasonic beam sector scan 223 toward the second end 22 of the inboard journal 20. As can be seen in FIG. 1, the second ultrasonic beam sector scan 223 provides coverage from before the first gear seat 26 well into the inboard journal 20 beyond the brake disk seat 38, providing coverage of the first gear seat anomaly 25, brake disk seat anomaly 27, and the inboard journal anomaly 29.

Figure 3:
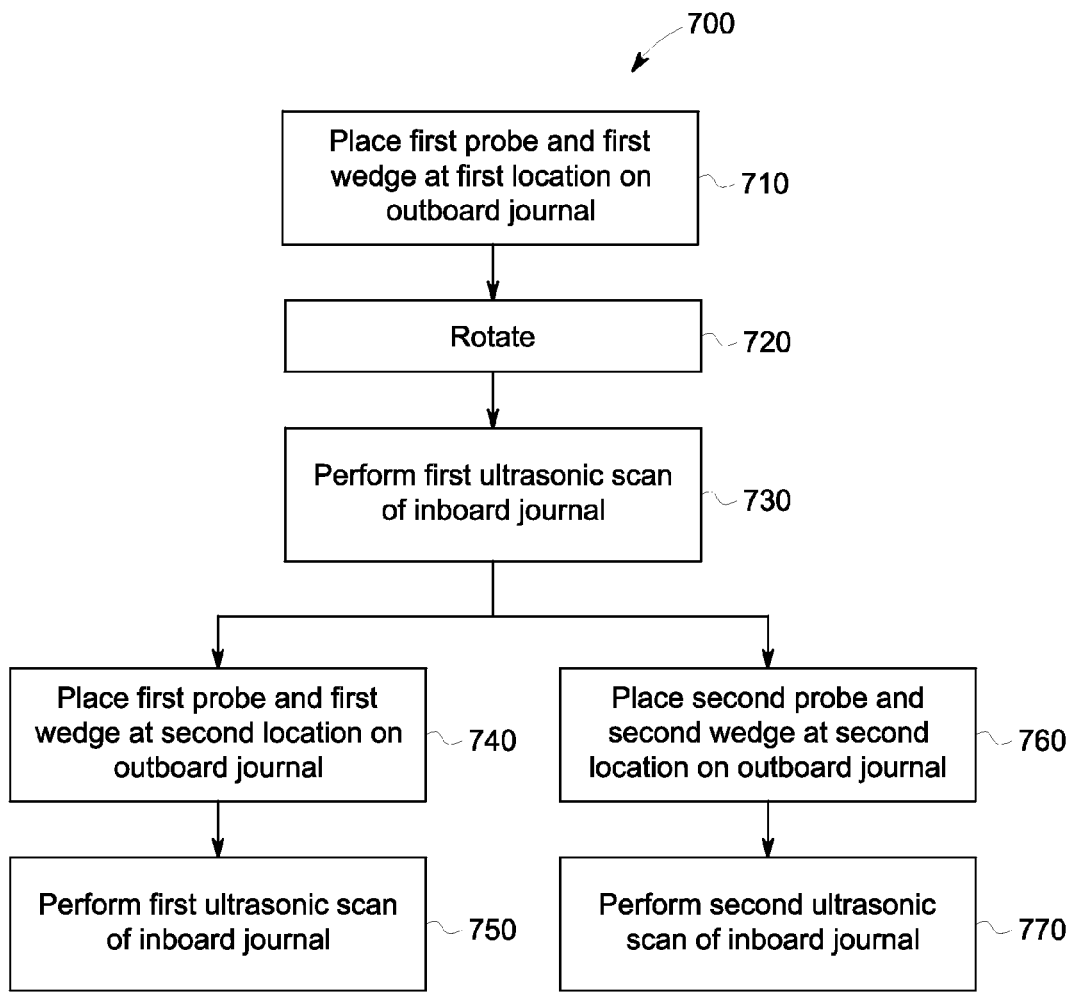
FIG. 3 is a flow diagram of an exemplary method for ultrasonic inspection of an axle.

FIG. 3 is a flow diagram 700 of an exemplary method for ultrasonic inspection of an axle 3. As shown in FIGS. 1 and 2, the axle 3 includes a longitudinal axis 5 and an inboard journal 20 between a first outboard journal 10 and a second outboard journal 50. The ultrasonic inspection can be conducted without having to remove or otherwise disassemble any of the devices mounted on the inboard journal 20, including the wheels 34, 74, gears 36, 76, brake disk 38, or cover 40. At step 710, the first ultrasonic probe 110 and the first ultrasonic wedge 114 are placed at a first ultrasonic wedge location 15 on the radial surface 16 of the first outboard journal 10. At step 720, the axle 3 is rotated by, e.g., rotating the wheels 34, 74 of the axle 3 using a roller stand 610 (FIG. 2). In another embodiment, axle 3 remains stationary while the ultrasonic probe 110 is rotated around the axle 3 using the ultrasonic probe manipulators 611 (FIG. 2). At step 730, a first ultrasonic scan directed to the inboard journal 20 is performed during rotation of the axle 3 or the probe 110. In one embodiment, the first ultrasonic probe 110 is a phased array ultrasonic probe, and the first ultrasonic scan is the first ultrasonic beam sector scan 123, wherein the first ultrasonic beam sector scan 123 is within a range between the lower first refracted ultrasonic beam 121 at a lower first refracted ultrasonic beam angle 131 of forty degrees and an upper first refracted ultrasonic beam 122 at an upper first refracted ultrasonic beam angle 132 of eighty degrees. In another embodiment, the first ultrasonic probe 110 is a single element probe, and the first ultrasonic scan is an A-scan.

If only a single probe and wedge are to be used to inspect the first end 1 of the axle 3 from the first outboard journal 10 and an additional ultrasonic scan of the inboard journal 20 is required, then at step 740, the first ultrasonic probe 110 and the first ultrasonic wedge 114 are placed at a second ultrasonic wedge location 17 on the radial surface 16 of the first outboard journal 10. In one embodiment, the first ultrasonic wedge location 15 is proximate to the distal end 11 of the first outboard journal 10 and the second ultrasonic wedge location 17 is proximate to the proximal end 12 of the first outboard journal 10, axially opposite of the distal end 11 of the first outboard journal 10. At step 750, a second ultrasonic scan directed to the inboard journal 20 is performed while the axle 3 is rotated.

If a second probe and wedge are to be used to inspect the first end 1 of the axle 3 from the first outboard journal 10 and an additional ultrasonic scan of the inboard journal 20 is required, then at step 760, a second ultrasonic probe 210 and a second ultrasonic wedge 214 are placed at the second ultrasonic wedge location 17 on the radial surface 16 of the first outboard journal 10. In one embodiment, the first ultrasonic wedge location 15 is proximate to the distal end 11 of the first outboard journal 10 and the second ultrasonic wedge location 17 is proximate to the proximal end 12 of the first outboard journal 10, axially opposite of the distal end 11 of the first outboard journal 10. At step 770, a second ultrasonic scan directed to the inboard journal 20 is performed while the axle 3 is rotated.

In view of the foregoing, embodiments of the method and system for ultrasonic inspection of an axle eliminates the need to remove or otherwise disassemble devices on the inboard journal of the axle. A technical effect is to simplify and reduce the time required to conduct the inspection.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for ultrasonic inspection of an axle, wherein the axle comprises a longitudinal axis and an inboard journal between a first outboard journal and a second outboard journal, and wherein a plurality of devices are mounted on the inboard journal, the method comprising the steps of:
   placing a first ultrasonic probe and a first ultrasonic wedge at a first location on a radial surface of the first outboard journal, wherein the radial surface is substantially parallel to the longitudinal axis of the axle;
   performing a first ultrasonic scan directed to the inboard journal;
   placing a second ultrasonic probe and a second ultrasonic wedge at a second location on the radial surface of the first outboard journal; and
   performing a second ultrasonic scan directed to the inboard journal,
   wherein the plurality of devices mounted on the inboard journal remain mounted during the second ultrasonic scan,
   wherein the plurality of devices mounted on the inboard journal remain mounted during the first ultrasonic scan.

2. The method of claim 1, wherein the first location is proximate to a first end of the first outboard journal and the second location is proximate to a second end of the first outboard journal, axially opposite of the first end of the first inboard journal.

3. The method of claim 1, wherein the first ultrasonic probe is a phased array ultrasonic probe.

4. The method of claim 3, wherein the first ultrasonic scan is a first ultrasonic beam sector scan.

5. The method of claim 4, wherein the first ultrasonic beam sector scan is within a range between a lower first refracted ultrasonic beam at a lower first refracted ultrasonic beam angle of forty degrees and an upper first refracted ultrasonic beam at an upper first refracted ultrasonic beam angle of eighty degrees.

6. The method of claim 1, wherein the parameters of the first ultrasonic scan are the same as the second ultrasonic scan.

7. The method of claim 1, wherein the first ultrasonic probe is a single element probe.

8. The method of claim 7, wherein the first ultrasonic scan is an A-scan.

9. The method of claim 1, further comprising the step of rotating the axle during the first ultrasonic scan.

10. A system for ultrasonic inspection of an axle, wherein the axle comprises a longitudinal axis and an inboard journal between a first outboard journal and a second outboard journal, and wherein a plurality of devices are mounted on the inboard journal, the system comprising:
   an ultrasonic inspection station comprising a display, a microprocessor, a memory coupled to the microprocessor, and one or more executable instructions stored in the memory and configured to be executed by the processor;
   a first ultrasonic probe and a first ultrasonic wedge at a first location on a radial surface of the first outboard journal, wherein the radial surface is substantially parallel to the longitudinal axis of the axle; and
   a first probe cable connecting the first ultrasonic probe to the ultrasonic inspection station,
   wherein the first ultrasonic probe and the first ultrasonic wedge are configured to perform a first ultrasonic scan directed to the inboard journal, and
   wherein the plurality of devices mounted on the inboard journal remain mounted during the first ultrasonic scan; and
   a second ultrasonic probe and a second ultrasonic wedge at a second location on the radial surface of the first outboard journal; and
   a second probe cable connecting the second ultrasonic probe to the ultrasonic inspection station,
   wherein the second ultrasonic probe and the second ultrasonic wedge are configured to perform a second ultrasonic scan directed to the inboard journal, and
   wherein the plurality of devices mounted on the inboard journal remain mounted during the second ultrasonic scan.

11. The system of claim 10, wherein the first ultrasonic probe is a phased array ultrasonic probe.

12. The system of claim 11, wherein the first ultrasonic scan is a first ultrasonic beam sector scan.

13. The system of claim 12, wherein the first ultrasonic beam sector scan is within a range between a lower first refracted ultrasonic beam at a lower first refracted ultrasonic beam angle of forty degrees and an upper first refracted ultrasonic beam at an upper first refracted ultrasonic beam angle of eighty degrees.

14. The system of claim 10, wherein the first ultrasonic probe is a single element probe.

15. The system of claim 14, wherein the first ultrasonic scan is an A-scan.

16. A method for ultrasonic inspection of an axle, wherein the axle comprises a longitudinal axis and an inboard journal between a first outboard journal and a second outboard journal, and wherein a plurality of devices are mounted on the inboard journal, the method comprising the steps of:

placing a first ultrasonic probe and a first ultrasonic wedge at a first location on a radial surface of the first outboard journal, wherein the radial surface is substantially parallel to the longitudinal axis of the axle;

performing a first ultrasonic scan directed to the inboard journal;

placing the first ultrasonic probe and the first ultrasonic wedge at a second location on the radial surface of the first outboard journal; and performing a second ultrasonic scan directed to the inboard journal, wherein the plurality of devices mounted on the inboard journal remain mounted during the second ultrasonic scan, wherein the plurality of devices mounted on the inboard journal remain mounted during the first ultrasonic scan.

17. The method of claim 16, wherein the first location is proximate to a first end of the first outboard journal and the second location is proximate to a second end of the first outboard journal, axially opposite of the first end of the first inboard journal.

18. The method of claim 17, wherein the parameters of the first ultrasonic scan are the same as the second ultrasonic scan.

\* \* \* \* \*